(12) United States Patent
Robillard et al.

(10) Patent No.: US 9,927,052 B1
(45) Date of Patent: Mar. 27, 2018

(54) SANITARY CLAMP WITH CONCEALED THREADS

(71) Applicant: Feldmeier Equipment, Inc., Syracuse, NY (US)

(72) Inventors: Tyler E. Robillard, Oswego, NY (US); Kyle A. Brown, Jamesville, NY (US)

(73) Assignee: Feldmeier Equipment, Incorporated, North Syracuse, NY (US)

( * ) Notice: Subject to any disclaimer, the term of this patent is extended or adjusted under 35 U.S.C. 154(b) by 0 days.

(21) Appl. No.: 15/345,717

(22) Filed: Nov. 8, 2016

(51) Int. Cl.
*F16L 23/10* (2006.01)
*F16L 23/18* (2006.01)

(52) U.S. Cl.
CPC ............... *F16L 23/10* (2013.01); *F16L 23/18* (2013.01)

(58) Field of Classification Search
CPC .................................. F16L 23/10; F16L 23/18
See application file for complete search history.

(56) References Cited

U.S. PATENT DOCUMENTS

| 2,689,141 | A | * | 9/1954 | Kiekhaefer | ............ F16L 23/06 24/279 |
| 3,534,988 | A | * | 10/1970 | Lindsey | ............ F16L 13/166 285/305 |
| 4,472,097 | A | | 9/1984 | Kiefer et al. | |
| 4,472,098 | A | | 9/1984 | Kiefer et al. | |
| 4,492,817 | A | | 1/1985 | Selby | |
| 4,671,546 | A | | 6/1987 | Arav | |
| 4,802,700 | A | * | 2/1989 | Stevenson | ............ F16B 21/078 292/327 |
| 4,887,950 | A | | 12/1989 | Sakayori et al. | |
| 5,098,241 | A | | 3/1992 | Aldridge et al. | |
| 5,553,984 | A | | 9/1996 | Smith | |
| RE35,358 | E | * | 10/1996 | Belser | ................ F16B 13/0808 411/342 |
| 5,653,481 | A | * | 8/1997 | Alderman | ............... F16B 31/04 24/279 |
| 6,244,807 | B1 | | 6/2001 | Garcia | |
| 6,305,889 | B1 | * | 10/2001 | Blessing | ................ F16B 39/34 411/353 |
| 6,347,708 | B1 | | 2/2002 | Ostergaard | |
| 6,708,984 | B1 | * | 3/2004 | North | ................... F16J 15/104 277/608 |

(Continued)

*Primary Examiner* — Robert Sandy
*Assistant Examiner* — David M Upchurch
(74) *Attorney, Agent, or Firm* — Bernhard P. Molldrem, Jr.

(57) ABSTRACT

A sanitary clamp with facing ring halves employs one or more threaded closure devices configured to avoid having any threads exposed to the ambient. A bolt member may have a stepped shaft with a first smooth shaft portion and a male-threaded tip portion. The latter may be the same or a smaller diameter. An associated nut member has a blind bore that extends from a first end of the nut, with a first smooth wall portion and a second female threaded bore portion. The second female threaded portion may have the same bore diameter, or the bore can have a stepped interior diameter with the second female threaded bore portion having a diameter smaller than the first smooth wall portion. A seal member or gland within the smooth wall bore portion closes off a space defined between said the tip portion of the bolt member and the female-threaded bore portion. Once installed, there are no threaded surfaces of the bolt member or the nut member that are exposed to the ambient.

12 Claims, 4 Drawing Sheets

(56) References Cited

U.S. PATENT DOCUMENTS

| | | |
|---|---|---|
| 7,077,611 B2 | 7/2006 | Metschke |
| 7,318,390 B2 | 1/2008 | Amy |
| 7,883,121 B2 | 2/2011 | Henry |
| 8,220,113 B2 | 7/2012 | Morton et al. |
| 8,240,718 B2 | 8/2012 | Morton et al. |
| 8,371,623 B2 | 2/2013 | Bronnert |
| 8,375,543 B1 * | 2/2013 | Balsells ............... F16L 37/084 267/167 |
| 2002/0109355 A1 * | 8/2002 | Elliott ...................... F16B 2/10 285/410 |
| 2002/0185869 A1 * | 12/2002 | Lin ...................... F16L 37/091 285/374 |
| 2005/0258648 A1 * | 11/2005 | Newman ............... F16L 23/10 285/364 |
| 2006/0197344 A1 * | 9/2006 | Henry .................... F16L 23/10 285/420 |
| 2007/0236008 A1 * | 10/2007 | Kim ...................... F16L 23/18 285/206 |

* cited by examiner

SANITARY CLAMP WITH CONCEALED THREADS

BACKGROUND OF THE INVENTION

This invention relates to equipment for sanitary clamps for joining two flanged tubes or pipes together in a way that seals the junction of the two flanged ends and which allows the tubes and associated equipment to be cleaned in place by an injection of a cleaning fluid. The invention is more particularly concerned with a sanitary clamp that employs a threaded closure, e.g., a bolt or an eyebolt and an associated wing nut or hex nut to secure the clamp onto the flanged tube ends, and which when screwed down onto the clamp has no exposed screw threads, which can harbor bacteria or other contaminants and which are difficult to clean.

There are a number of styles of sanitary clamps which go by names such as tri-clamp, C-clamp, tri-clover, ferrule, sanitary ferrule, hygienic clamp, hygienic clamp ferrule, and hygienic clamp union.

Over the past decade sanitary piping and sanitary vessels have received a great deal of scrutiny of their product design and the quality of finishes to optimize cleanability. Clamps of the type described have facilitated the cleaning of the interior of the sanitary flow line and any associated vessel or component. However, in more recent years this scrutiny has been extended to the outside of piping and the outside of vessels, that is, to the entire clean area, including the exterior of the sanitary lines. Some sanitary lines including piping and vessels are now installed in clean manufacturing environments, i.e., clean rooms, where airborne particulate contamination has to be monitored and controlled. The response to this has been to improve the finishes and design of external components so they can be cleaned. Despite the increased interest in hygienic designs and avoiding structures and surfaces that may collect and harbor contaminates, there have been no major changes to the designs of sanitary clamps, which continue to be offered only with exposed threads.

Equipment located in clean areas of food, dairy, or pharmaceutical processing or other comestible liquid processing environments are required to be cleaned periodically by wash-down, or manually cleaned by wipe-down with harsh cleaning solutions, i.e., caustics. All components of the food or other sanitary processing line have to be capable of being chemically cleaned or steam cleaned, and then rinsed in a pressure wash.

Despite these requirements, designs for the sanitary clamp itself still employ closures with exposed threads which are notorious for collecting and harboring bacteria. Often a valve cluster or other processing equipment may have many sanitary clamps, which currently all have one or two bolt closures where there are exposed threads. This possible source of contamination in the clean environment has been overlooked and there has been no effort made to address it. These sanitary clamps employ either an eyebolt (swing bolt) and a wing nut or two common bolts and wing nuts or hex nuts, depending on the design. In either case these are fully threaded, and the wing nuts and hex nuts are of designs that leave their internal female threads exposed to the ambient, as well of the male threads of the threaded bolt shafts.

With this construction it is not possible for all external exposed surfaces to be completely cleaned by washing it and rinsing it with a cleaning fluid, because of the difficulty in cleaning the threads. Any screw threads would have to be sealed off and isolated from any contact with the ambient atmosphere, but this issue has been completely overlooked in the sanitary clamp art.

OBJECTS AND SUMMARY OF THE INVENTION

It is an object of the present invention to provide an aseptic, sanitary, or hygienic clamp of straightforward construction, but with a closure designed to capable of being cleaned and with no threaded surfaces that are exposed to the ambient, so as to avoid the drawbacks, as previously mentioned, that affect the sanitary clamps of the prior art.

It is another object to provide an aseptic, sanitary, or hygienic clamp that can be easily installed and where the required bolts and nuts can be interchanged with those on existing sanitary clamps.

According to one aspect of the invention, a sanitary clamp has an annulus or ring formed of facing ring halves, each ring half with an annular channel to fit over the flanges of a pair of flanged round members, such as flanged tube ends or a flanged end cap and a flanged tube. The ring halves each are also formed so as to have a jaw in the form of a radially protruding finger, with a bolt slot, with the finger extending radially out from the associated ring half. The ring halves can be hinged to close together, or they can have the extending fingers on both sides so they are held together with a bolt and nut on each side. These are pulled together to close up the facing pair of flanged round members. Typically a gasket or gland is placed between tube ends to ensure the tube ends are in sealed engagement with one another.

A bolt member is configured to penetrate the fingers (e.g., through the bolt slot) for closing them towards one another. The bolt member has a head (which can be a ring or eye, or can be a hex head, for example) and a shaft or shank. The shaft has a first smooth shaft portion extending from the head, with a smooth unthreaded wall surface and a first predetermined diameter. Then there is a male-threaded tip portion extending from the smooth shaft portion and aligned coaxial with it. This tip portion has a male spiral thread thereon, and in some embodiments may be necked down or reduced, i.e., so it has a second diameter smaller than the first diameter, i.e., smaller than the diameter of the smooth first shaft portion. In other embodiments, the smooth shaft portion and the threaded tip may have the same diameter. The cooperating nut member is designed to thread onto this bolt member and draw the finger members towards one another to bring the ring halves into sealing engagement with the flanged tube ends. The nut member has a blind bore that extends from a first end of the nut, and does not penetrate out the other end. This blind bore has a first smooth wall portion of a first predetermined bore diameter corresponding with the diameter of the bolt's smooth shaft portion, to admit entry of the smooth shaft portion, and then has a second female-threaded bore portion extending coaxial with the first smooth wall bore portion with a diameter to match the tip of the bolt member. In some embodiments, this means the threaded bore portion has a diameter smaller than the first predetermined bore diameter. This portion is designed and adapted for making threaded engagement with the tip portion of the bolt member.

In order to ensure that all the threads are concealed and no threads are exposed, the bore of the nut is open only at said first end of the nut member, and a seal member or gland, e.g., a ring seal or O-ring, is disposed within the first smooth wall bore portion of the nut member adjacent said free end. When the nut member is installed onto the bolt member, this seal ring closes off a space that contains the tip portion of the bolt member and the female threaded bore portion. Thus, there are no threads of the bolt member or of the nut member that are exposed to the ambient. Consequently, the remaining exposed surfaces, free of threads, can be easily cleansed of any microbial contaminates.

Depending on the design the nut member can take the form of a wing nut having a pair of radially protruding wing members, or may take the form of a hex nut having a plurality of engaging surfaces on a its circumference or in a central recess in some cases. Other types of nuts are possible, such as those that accept an allen wrench, or another wrench or key.

The bolt member shaft has a first smooth shaft portion extending from the head, with a smooth unthreaded wall surface and a first predetermined diameter. A male-threaded tip portion extends from the smooth shaft portion and aligns coaxially with it. This tip portion has a male spiral thread thereon, and in some embodiments may be shouldered or necked down to a second diameter smaller than the first diameter, that is, the diameter of the smooth first shaft portion. The cooperating nut member is designed to thread onto this bolt member, with a blind bore that extends from a first end of the nut, and does not penetrate out the other end. This blind bore has a first smooth wall portion of a first predetermined bore diameter corresponding with the diameter of the bolt's smooth shaft portion, to admit entry of the smooth shaft portion, and then has a second female-threaded bore portion extending coaxial with the first smooth wall bore portion and having a diameter to correspond to the tip portion of the bolt member. In some cases this would be smaller than the first predetermined bore diameter. The tip portion makes threaded engagement with the tip portion of the bolt member. The O-ring, annular seal gland, or other sealing gasket or gland can be disposed in an annular cutout formed in the wall of the blind bore near the opening, so all threads are concealed from the environment once the nut is installed and tightened down onto the shaft. Alternatively, the seal member may be positioned in a recess on the smooth shaft portion of the bolt member.

The above and many other objects, features, and advantages of the arrangements of the present invention will become apparent from the ensuing detailed description of preferred embodiments of the invention, when read in connection with the accompanying Drawing.

DETAILED DESCRIPTION OF THE PREFERRED EMBODIMENT

Figure 1:
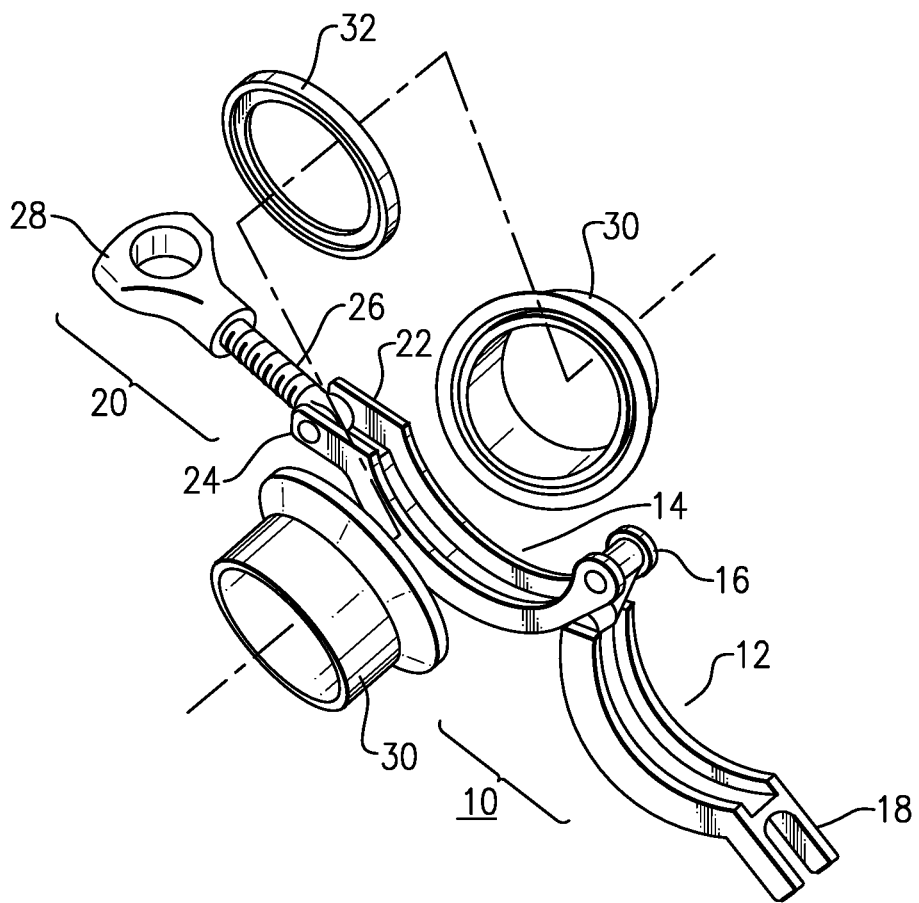
FIG. 1 is perspective view of an example of sanitary clamp according to the prior art, shown open to explain its general construction.
Figure 2:
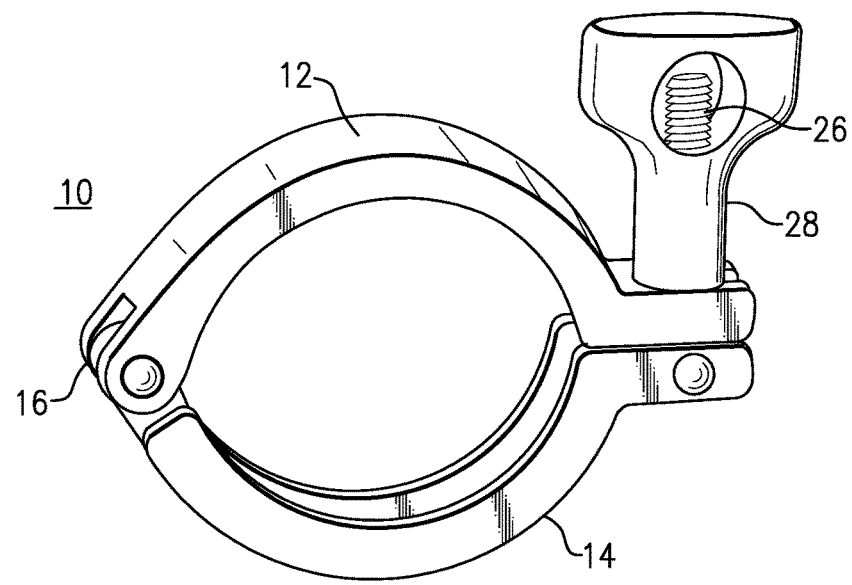
FIGS. 2 and 3 are perspective views of sanitary clamps according to the prior art.
Figure 3:
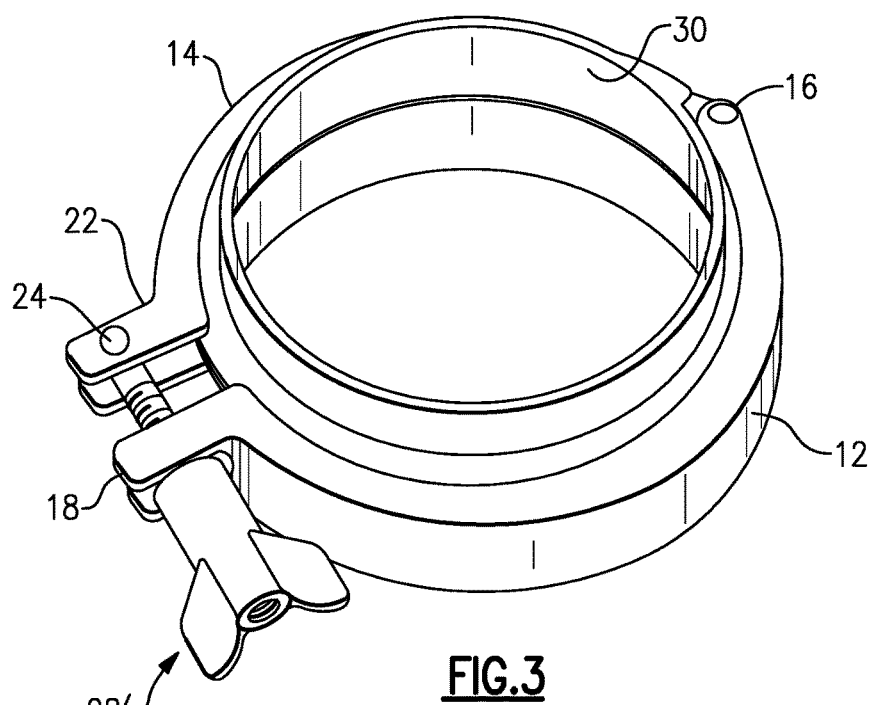

With initial reference to FIGS. 1 to 3, a sanitary clamp, i.e., a standard C-clamp or tri-clamp 10 of the prior art is presented as a standard device for joining pipe ends for processing equipment joined to a sanitary conduit, for example in a process for a dairy product, another edible product such as fruit juice, sauce or soup, or a pharmaceutical product for human or veterinary use, or a cosmetic, beauty-related, or dermatological creme or liquid. Typically there are many of these sanitary clamps employed in any commercial processing operation of this type.

The sanitary clamp 10 of this example has first and second ring halves 12 and 15 joined at proximal ends at a clamp hinge member 16, with an open jaw member 18 projecting as a radial finger from the proximal end of the ring half 12, with a bolt slot 19 extending along the jaw member 18. A threaded closure member 20, here a swing bolt 26 or eye bolt 26, has a head or eye captured on a pivot pin or hinge pin 24 to attach it into a bolt slot of a radial finger 22 at the proximal end of the other ring half 14. In this case the swing bolt or eye bolt 26 is threaded along the entire length of the shaft, and a thumb screw or wing nut 28 is threaded onto the shaft and turned down to clamp the C-clamp or tri-clamp closed.

As shown in FIG. 1, this clamp is used to hold together a pair of flanged tube ends 30, with a seal or gland 32 placed between them. The flanges are captured in an annular channel formed in the two ring halves 12 and 14.

FIG. 2 shows the clamp 10 closed together, but not installed on sanitary tubing. This view shows that the wing nut 28 leaves the threads the bolt shaft 26 open to the environment.

FIG. 3 shows a similar C-clamp 28' in place on a pair of tube ends 30, with the wing nut 28' turned down to hold the wing nut in place against the jaw or radial finger 18. In this case the wing nut 28' is a different style from the wing nut 28 of FIG. 1, with a bore extending the length of the nut, and thus with the male threads of the bolt and the female threads of the wing nut 28' both exposed to the ambient and being a possible place where contaminates can collect.

Figure 4:
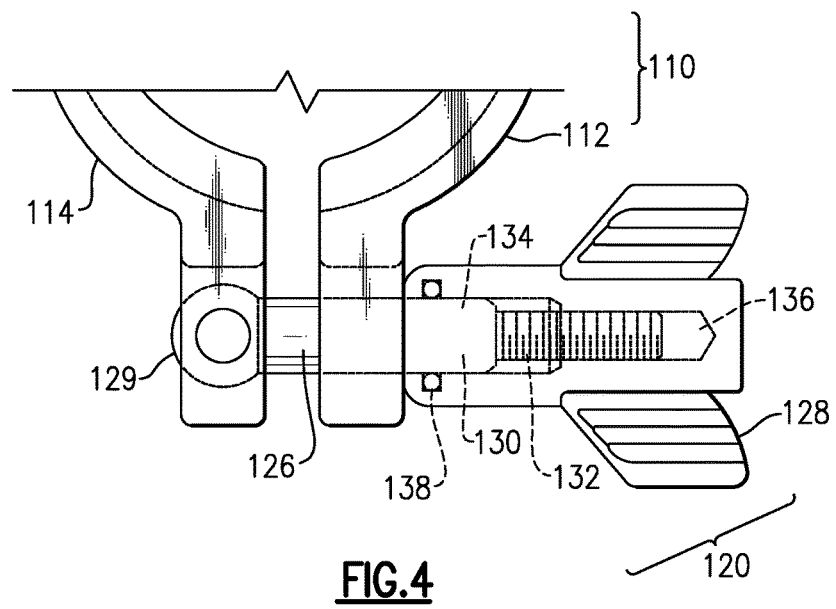
FIG. 4 is a partial elevational view of the a sanitary clamp according to one exemplary embodiment of this invention, showing portions of the bolt and nut in broken line.
Figure 5:
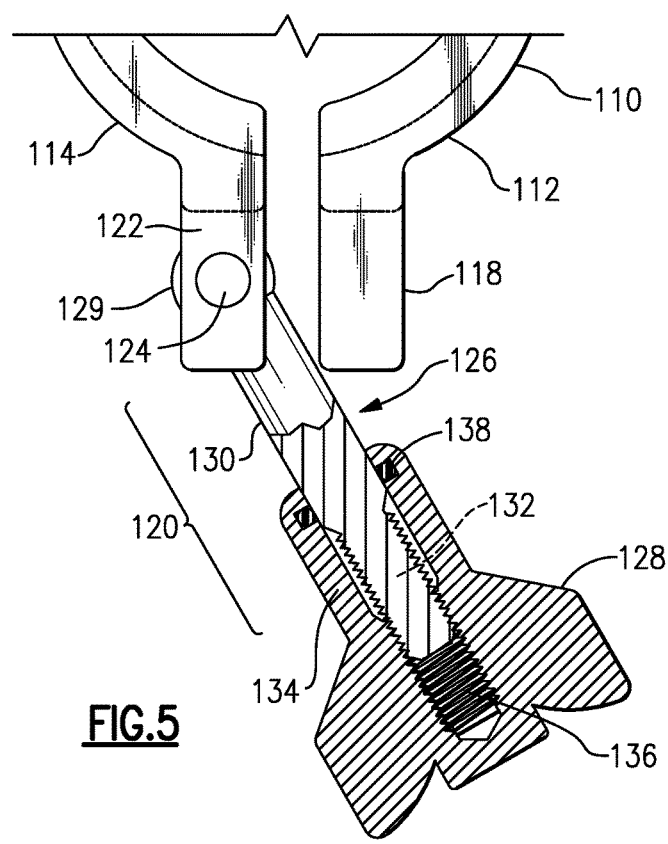
FIG. 5 is another elevational view thereof showing a portion of the bolt shaft and the associated nut in cross-section.

The improvement of the present invention can be explained with reference to the embodiment illustrated in FIGS. 4 and 5. Here, the general structure of the C-clamp or tri-clamp 110 is similar to the prior-art embodiment of FIGS. 1 and 2, and elements similar to those in the sanitary clamp of FIGS. 1-3 are identified by the same reference numbers, but raised by 100, and a detailed description can be omitted. The improvement here lies in the threaded fastener or closure 120, with a stepped swing bolt 126 and wing nut 128. The swing bolt 126 has a head or eye member 129 that is captured on a pivot pin 124 in the radially extending jaw or finger 122. The eye bolt or swing bolt 126 is of stepped construction, with a first smooth wall portion 130 of the shaft extending out from the eye or head 129 and a second, male-threaded tip portion 132. The tip member is stepped down, having a diameter smaller than the diameter of the first portion 130. In other embodiments, as discussed later, the shaft may be un-stepped, with the second, male-threaded tip portion having the same diameter as the first smooth-wall portion.

The corresponding wing nut 128 has a blind, partly threaded bore 134, with a relatively wide initial portion 135 extending from the open end of the bore. This portion 135 has a predetermined diameter to approximately match the predetermined diameter of the smooth wall portion 130 of the bolt shaft. A narrower interior tip portion 16 of the wing nut bore continues from the end of the portion 135 along the same axis, and ends without penetrating the far end of the nut. This portion 136 has female threads to match the male threads of the tip portion 132 of the associated swing bolt.

To isolate the male and female threads of the tip portions 132 and 136 from the ambient, a seal ring 138, e.g., an O-ring seal or equivalent annular seal gland is situated in an annular cut out 139 adjacent the open end of the bore. As shown, with the wing nut 128 in place on the bolt 126, the seal ring 138 bears upon the smooth, unthreaded wall surface of the larger diameter portion 130 of the bolt, and effectively conceals all threads from the ambient. For embodiments employing a bolt with un-stepped shaft, the bore would have the threaded tip portion with approximately the same diameter as the smooth portion, allowing for the lands and grooves of the female threads.

The construction of the swing bolt and nut is simple, but robust, without requiring complex shapes, and the bolt can be changed out to replace a standard swing bolt in an existing sanitary clamp of the type shown in FIGS. 1 to 3. Thus, these improved clamps and closures are relatively inexpensive to manufacture, and simple to install and maintain.

Figure 6:
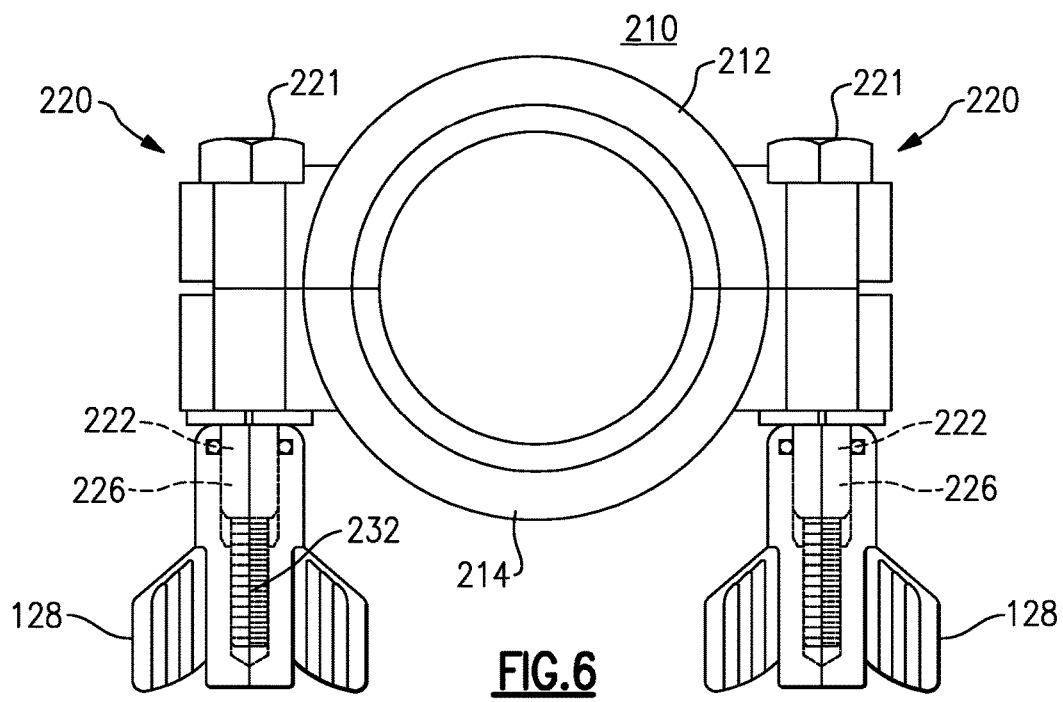
FIG. 6 illustrates a sanitary clamp according to another embodiment of the invention.

An alternative construction for the sanitary clamp is shown in FIG. 6, in which the clamp 210 is formed of a pair of mating ring halves 212 and 214 which are held together using a pair of threaded fastener devices 220, 220 one at each end of the facing ring halves. In this embodiment the fasteners each have a bolt member with a hex head 221 affixed on to the shaft 222, with the shaft having a larger-diameter smooth wall portion 226 and a smaller diameter threaded tip portion 232. The bolts are adapted to mate with the blind-bore wing nuts 128 of the type employed in the embodiment of FIGS. 4 and 5.

Figure 7:
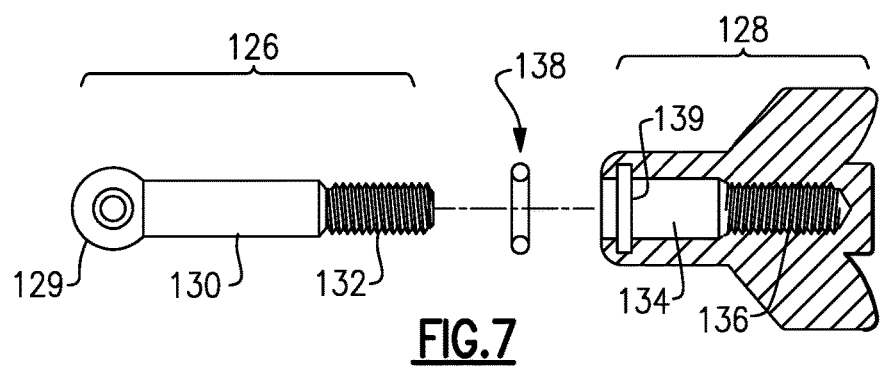
FIGS. 7 and 8 are examples of bolts and mating nut members that embody the present invention.
Figure 8:
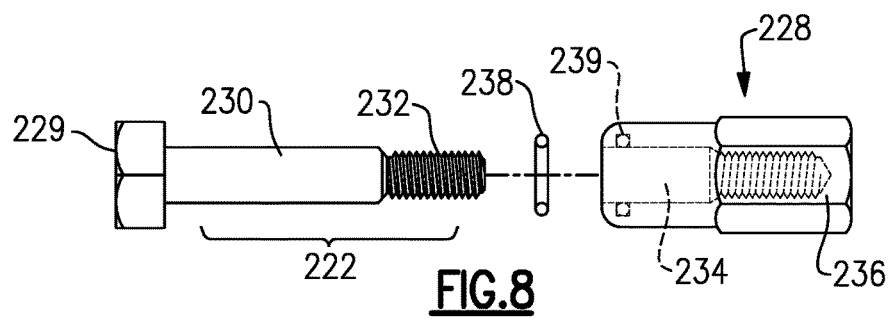

Alternative constructions for the threaded fasteners, apart from the sanitary clamps, are illustrated in FIGS. 7 and 8.

FIG. 7 shows the bolt member 126 with an eye or pivot head 129, and a shaft with its initial smooth, unthreaded shaft portion 130 and a smaller diameter threaded tip portion 232, and with the associated wing nut 128 with the blind bore having an wide, smooth wall bore portion (provided without threads) 134 and smaller diameter female threaded tip portion 136 that does not penetrate the end of the nut. As described earlier, a seal ring 138 is seated into an annular seat 139 formed near the opening of the bore.

FIG. 8 illustrates alternative construction of a generally equivalent threaded fastener arrangement with a bolt member having a hex head 229, a shaft 222 extending from the head and having a first, larger diameter smooth wall shaft portion 230 and a smaller-diameter male-threaded tip portion 232. Here, a hex nut 228 has a plurality of flat grip surfaces to accept a wrench or a hex drive to turn the nut on the bolt. As in the other embodiment(s), the nut has a stepped-diameter blind bore with a first, wider-diameter smooth wall portion 234 and a narrower-diameter female threaded tip portion 236.

The two styles of nut 128 and 228 are interchangeable, and not specific to any bolt type.

An O-ring seal has been used in the foregoing examples, but there are many other seals and glands which are familiar in the art and which could be easily employed in other embodiments, for keeping threaded surfaces behind a seal in sanitary clamps or other applications.

While the invention has been described with reference to a number of preferred embodiments, it should be understood that the invention is not limited only to those embodiments. Rather many variations are possible without departing from the scope and spirit of this invention, as defined in the appended Claims.

What is claimed is:

1. Sanitary clamp comprising
    a ring formed of facing ring halves, each ring half having a radially protruding finger that extends out from the associated ring half, the ring halves being adapted for closing together onto a pair of flanged round members for holding the round members in sealed engagement with one another;
    a bolt member adapted to penetrate said fingers in proximity to one another, the bolt member having a head and a shaft that includes a first smooth shaft portion extending from said head having a smooth unthreaded wall surface and a first predetermined diameter, and a male-threaded tip portion extending from said smooth shaft portion and coaxial with it, with a male spiral thread thereon, and having a second diameter; and
    a nut member for threadably engaging said bolt member and drawing said finger members towards one another to bring the ring halves into sealing engagement with said flanged round members; the nut member having a blind bore extending from a first end of the nut, the blind bore having a first smooth wall portion of a first predetermined bore diameter to admit entry of the first smooth shaft portion of said bolt member, and a second female threaded bore portion extending coaxial with the first smooth wall bore portion and having a predetermined diameter and having a female spiral thread adapted for threaded engagement with the tip portion of said bolt member, said bore being open only at said first end of the nut member; and
    a seal member disposed within said first smooth wall bore portion of said nut member adjacent said free end, such that once said nut member is fastened onto said bolt member, said seal member closes off a space defined between said the tip portion of said bolt member and the female threaded bore portion, such that the male and female spiral threads of the bolt member and the nut member are entirely concealed.

2. The sanitary clamp according to claim 1 wherein said seal member comprises an annular seal member fitted into an annular seat formed in the first smooth wall bore portion.

3. The sanitary clamp according to claim 1 wherein said nut is in the form of a wing nut having a pair of wing members protruding radially therefrom.

4. The sanitary clamp according to claim 1 wherein said nut has a head that includes a plurality of flat engaging surface adapted to fit a wrench or driver.

5. The sanitary clamp according to claim 1 wherein said nut is in the form of a hex nut having a plurality of flat engaging surfaces on a circumference thereof.

6. The sanitary clamp according to claim 1 wherein said second diameter is smaller than said first diameter.

7. The sanitary clamp according to claim 6 wherein said male-threaded tip portion of said bolt member is necked down from said first smooth shaft portion.

8. A threaded fastener assembly for use in an environment in which threads exposed to the ambient must be avoided, comprising
    a bolt member having a head and a shaft that includes a first smooth shaft portion extending from said head having a smooth unthreaded wall surface and a first predetermined diameter, and a male-threaded tip portion extending from said smooth shaft portion and coaxial with it, with a male spiral thread thereon, and having a second diameter;
    a nut member configured for threadably engaging said bolt member and having a blind bore extending from a first end of the nut, the blind bore having a first smooth wall portion of a first predetermined bore diameter to admit entry of the first smooth shaft portion of said bolt member, and a second female-threaded bore portion extending coaxial with the first smooth wall bore portion and having a diameter smaller than said first predetermined bore diameter and having a female spiral thread adapted for threaded engagement with the tip portion of said bolt member, said bore being open only at said first end of the nut member; and a seal member disposed within said first smooth wall bore portion of said nut member adjacent said free end, such that once said nut member is fastened onto said bolt member, said seal member closes off a space defined between said the tip portion of said bolt member and the female threaded bore portion, such that the male and female spiral threads of the bolt member and the nut member are entirely concealed.

9. The threaded fastener assembly according to claim 8, wherein said seal member includes a seal ring, and said nut member has an annular seal seat disposed in the blind bore adjacent an open end of the bore, with the seal ring being seated in said annular seal seat.

10. The threaded fastener assembly according to claim 8 wherein said nut member is in the form of a wing nut having a plurality of wings projecting therefrom.

11. The threaded fastener assembly according to claim 8 wherein said nut member has an arrangement of surfaces adapted to accept a wrench or hex driver.

12. The threaded fastener assembly according to claim 8, wherein said second diameter of said tip portion is smaller than said first diameter of said smooth shaft portion of said bolt member, and the diameter of said second female-threaded bore portion is smaller than said first predetermined bore diameter of said nut member.

* * * * *